United States Patent [19]
Leyendecker et al.

[11] Patent Number: 5,212,194
[45] Date of Patent: May 18, 1993

[54] PHENOXYALKYL-SUBSTITUTED HETEROAROMATICS AND A METHOD FOR CONTROLLING PESTS

[75] Inventors: Joachim Leyendecker, Ladenburg; Hans-Juergen Neubauer, Muenster-Hiltrup; Uwe Kardorff, Mannheim; Christoph Kuenast, Otterstadt; Wolfgang Krieg, Weingarten; Peter Hofmeister, Neustadt, all of Fed. Rep. of Germany

[73] Assignee: BASF Aktiengesellschaft, Ludwigshafen, Fed. Rep. of Germany

[21] Appl. No.: 658,241

[22] Filed: Feb. 20, 1991

Related U.S. Application Data

[62] Division of Ser. No. 379,956, Jul. 14, 1989, Pat. No. 5,013,847.

[30] Foreign Application Priority Data

Jul. 29, 1988 [DE] Fed. Rep. of Germany ....... 3825821
Jul. 29, 1988 [DE] Fed. Rep. of Germany ....... 3825822

[51] Int. Cl.$^5$ .................. C07D 261/08; A01N 43/80
[52] U.S. Cl. ..................................... 514/378; 548/247
[58] Field of Search .................. 548/247; 514/378

[56] References Cited

U.S. PATENT DOCUMENTS 4,625,036 11/1986 Boyle .................. 548/262

FOREIGN PATENT DOCUMENTS 0086043 8/1983 European Pat. Off. .
58-128380 7/1983 Japan .

Primary Examiner—Robert Gerstl
Attorney, Agent, or Firm—Oblon, Spivak, McClelland, Maier & Neustadt

[57] ABSTRACT

Phenoxyalkyl-substituted heteroaromatics of the formulae Ia and Ib

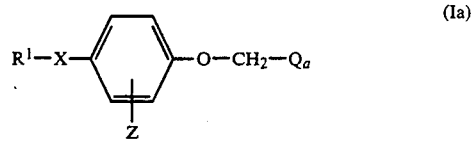

(Ia)

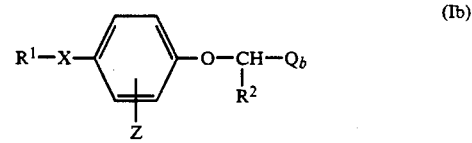

(Ib)

where the substituents have the following meanings:
$R^1$ $C_1$–$C_{12}$-alkyl, $C_2$–$C_{12}$-alkenyl, $C_2$–$C_{12}$-alkynyl, $C_1$–$C_{12}$-haloalkyl, $C_2$–$C_{12}$-haloalkenyl, $C_2$–$C_{12}$-haloalkynyl, $C_3$–$C_{12}$-alkoxyalkyl, $C_3$–$C_8$-cycloalkyl, $C_4$–$C_{12}$-cycloalkylalkyl, $C_3$–$C_8$-halocycloalkyl, $C_4$–$C_{12}$-halocycloalkylalkyl, $C_4$–$C_{12}$-cycloalkylhaloalkyl or $C_4$–$C_{12}$-halocycloalkylhaloalkyl;

Z hydrogen, halogen, $C_1$–$C_8$-alkyl, $C_1$–$C_8$-alkoxy, $C_1$–$C_4$-haloalkyl, $C_1$–$C_4$-haloalkoxy, $C_3$–$C_{10}$-cycloalkyl, nitro or cyano in the case of Ia and hydrogen, halogen, or $C_1$–$C_4$-alkyl in the case of Ib;

X O, S, SO$_2$;

$Q_a$ substituted or unsubstituted azole;

$Q_b$ substituted or unsubstituted heteroaromatic;

methods of manufacturing compounds Ia and Ib, and their use for combating pests.

6 Claims, No Drawings

PHENOXYALKYL-SUBSTITUTED HETEROAROMATICS AND A METHOD FOR CONTROLLING PESTS

This is a division of application Ser. No. 07/379,956, filed on Jul. 14, 1989 U.S. Pat. No. 5,013,847.

The present invention relates to novel phenoxyalkyl-substituted heteroaromatics of the general formulae Ia and Ib

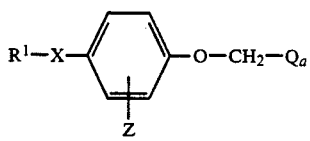
(Ia)

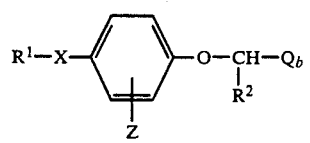
(Ib)

where $R^1$ is $C_1$–$C_{12}$-alkyl, $C_2$–$C_{12}$-alkenyl, $C_2$–$C_{12}$-alkynyl, $C_1$–$C_{12}$-haloalkyl, $C_2$–$C_{12}$-haloalkenyl, $C_2$–$C_{12}$-haloalkynyl, $C_3$–$C_{12}$-alkoxyalkyl, $C_3$–$C_8$-cycloalkyl, $C_4$–$C_{12}$-cycloalkylalkyl, $C_3$–$C_8$-halocycloalkyl, $C_4$–$C_{12}$-halocycloalkylalkyl, $C_4$–$C_{12}$-cycloalkylhaloalkyl or $C_4$–$C_{12}$-halocycloalkylhaloalkyl, X is O, S or $SO_2$, Z is hydrogen, halogen, $C_1$–$C_8$-alkyl, $C_1$–$C_8$-alkoxy, $C_1$–$C_4$-haloalkyl, $C_1$–$C_4$-haloalkoxy, $C_3$–$C_{10}$-cycloalkyl, nitro or cyano in the case of the heteroaromatic $Q_a$, and is hydrogen, halogen or $C_1$–$C_4$-alkyl in the case of the heteroaromatic $Q_b$, $R^2$ is hydrogen or $C_{1\text{-}4}$-alkyl, $Q_a$ is an unsubstituted or substituted azole radical of the formula IIa–IIf

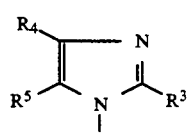
(IIa)

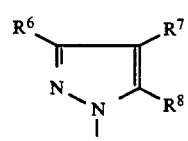
(IIb)

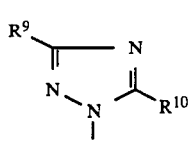
(IIc)

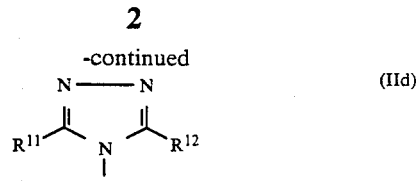
(IId)

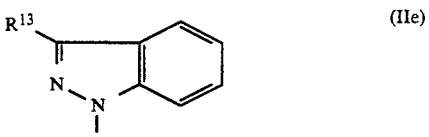
(IIe)

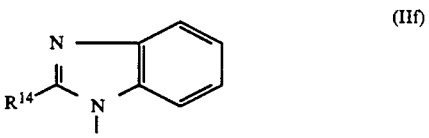
(IIf)

where $R^3$ to $R^{14}$ are each hydrogen, halogen, $C_1$–$C_8$-alkyl, $C_1$–$C_4$-haloalkyl, $C_1$–$C_4$-alkoxy, $C_3$–$C_{10}$-cycloalkyl or aryl which is unsubstituted or monosubstituted to trisubstituted by halogen, $C_1$–$C_8$-alkoxy, $C_1$–$C_4$-haloalkyl or $C_1$–$C_4$-haloalkoxy, and $Q_b$ is a 5-membered heteroaromatic which is bonded via a carbon atom and is unsubstituted or monosubstituted or polysubstituted by halogen, $C_1$–$C_8$-alkyl, $C_2$–$C_8$-alkenyl, $C_1$–$C_4$-haloalkyl, $C_1$–$C_8$-alkoxy, $C_1$–$C_8$-alkylthio, $C_2$–$C_8$-alkoxyalkyl or $C_3$–$C_{10}$-cycloalkyl.

The present invention furthermore relates to pesticides which contain the compounds Ia and Ib as active ingredients, and a method for controlling pests.

EP-A-132 606 discloses N-substituted azoles as insecticidal and acaricidal active ingredients. However, the action of these compounds is unsatisfactory.

EP-A 0 203 798 describes, for example, 1,3-thiazole which is phenoxyethoxy-substituted in the 2-position, of the structure A $(H_3C)_2HC-H_2C-H_2C-O-\phantom{X}-O-CH_2-CH_2-O-\underset{N}{\overset{S}{\diagdown\diagup}}\bigg]$ (A)

Phenoxymethyl-substituted heteroaromatics are disclosed in DE-A 25 16 331 and EP-A 239 047. The insecticidal action of these compounds is also unsatisfactory.

It is an object of the present invention to provide novel phenoxyalkyl-substituted heteroaromatics Ia and Ib having an improved action.

We have found that this object is achieved by the novel phenoxyalkyl-substituted heteroaromatics defined at the outset, and processes for their preparation.

We have also found that the compounds Ia and Ib are very suitable for controlling pests.

The compounds Ia and Ib are obtainable by the following methods:

For example, a phenol III is reacted with an N-methylazole IVa or with a heteroaromatic IVb having a 5-membered ring, in the presence of a base at from (−20°) to 250° C., preferably from 20° to 120° C., in accordance with the following equations:

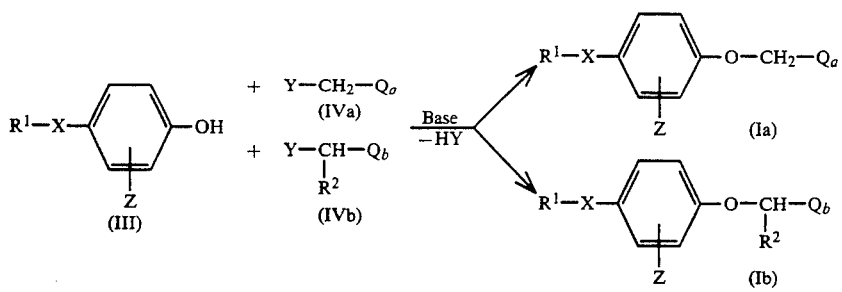

Some of the phenols III are known from Houben/Weyl, Vol. VI, 3, Methoden der organischen Chemie, Thieme Verlag, 1965, page 49 et seq. and 85 et seq., or can be prepared by the methods described there.

Some of the N-methylazoles IVa are disclosed in Heterocycles 24 (1986), 2233-2237, or can be prepared by the method described there, in accordance with the following equation:

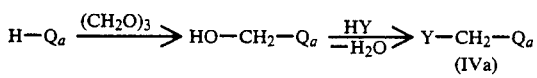

The heteroaromatics IVb are either known and are in some cases commercially available or can be prepared by generally known chemical processes. Processes for the preparation of thiophene derivatives are described in, for example, Comprehensive Heterocyclic Chemistry, A. R. Katritzky and C. W. Rees, Vol. 4, page 863 et seq., Pergamon Press, 1984; those for the preparation of furan derivatives are described in, for example, DE-A 35 14 384, DE-A 35 46 371 or Advances in Heterocyclic Chemistry, 30 (1982), page 167 et seq.; those for the preparation of pyrrole derivatives are described in, for example, Comprehensive Heterocyclic Chemistry, A. R. Katritzky and C. W. Rees, Vol. 4, page 313 et seq., Pergamon Press, 1984; those for the preparation of thiazole derivatives, oxazole derivatives, isothiazole derivatives, thiadiazole derivatives and oxadiazole derivatives are described in, for example, Comprehensive Heterocyclic Chemistry, A. R. Katritzky and C. W. Rees, Vol. 6, pages 131, 177, 235, 447 and 365 et seq., Pergamon Press, 1984; those for the preparation of imidazole derivatives are described in, for example, Advances in Heterocyclic Chemistry, 27 (1980), 242 et seq.; those for the preparation of pyrazole derivatives are described in, for example, Heteroaromatic Nitrogen Compounds, The Azoles, page 31 et seq., Cambridge University Press, 1976; those for the preparation of triazole derivatives are described in, for example, Comprehensive Heterocyclic Chemistry, A. R. Katritzky and C. W. Rees, Vol. 5, page 669 et seq., Pergamon Press, 1984, and those for the preparation of isoxazole derivatives are described in, for example, DE-A 25 49 962 and DE-A 27 54 832.

Usually, not less than an equivalent amount of a base is added to III and/or IVa or IVb, but the base may also be used in excess or, if necessary also as a solvent.

Examples of suitable bases are hydroxides of alkali metals and alkaline earth metals, such as sodium hydroxide, potassium hydroxide and calcium hydroxide, alcoholates of alkali metals and alkaline earth metals, such as sodium methylate, sodium ethylate, calcium methanolate or potassium tert-butylate, alkali metal or alkaline earth metal hydrides, such as sodium hydride, potassium hydride or calcium hydride, alkali metal or alkaline earth metal carbonates, such as sodium carbonate, potassium carbonate or calcium carbonate, aliphatic amines, such as dimethylamine, triethylamine or diisopropylamine, heterocyclic amines, such as piperidine, piperazine or pyrrolidine, aromatic amines, such as pyridine or pyrrole, and, if desired, also alkyllithium compounds, such as n-butyllithium.

The reaction is advantageously carried out in a solvent or diluent. Examples of suitable solvents or diluents are aliphatic hydrocarbons, such as n-pentane, n-hexane, the hexane isomer mixture and petroleum ether, aromatic hydrocarbons, such as benzene, toluene, the xylenes and their isomer mixtures, and gasoline, alcohols, such as methanol, ethanol, n-propanol and isopropanol, ethers, such as diethyl ether, di-n-butyl ether, methyl tert-butyl ether, tetrahydrofuran and dioxane, ketones, such as acetone, methyl ethyl ketone and methyl isopropyl ketone, nitriles, such as acetonitrile and propionitrile, and aprotic dipolar solvents, such as dimethylformamide, dimethyl sulfoxide or pyridine. Mixtures of these substances can also be used as solvents and diluents.

Instead of the phenol III plus the base, it is also possible to react the phenolate anion of III directly with IVa or IVb. In this case, the reaction temperatures are from $-20°$ to $120°$ C., preferably from $-20°$ to $80°$ C.

The anions of the phenols III are known in the form of their metal salts, such as sodium or potassium salt, or can be generated in situ from phenols III by reaction with conventional metallization reagents described in, for example, Houben/Weyl (see above), such as sodium methylate, sodium ethylate, potassium tertbutylate, sodium hydride, potassium hydride or n-butyllithium.

The reaction is advantageously carried out in a solvent or diluent. Examples of suitable solvents or diluents are aliphatic hydrocarbons, such as n-pentane, n-hexane, the hexane isomer mixture and petroleum ether, halohydrocarbons, such as chlorobenzene, methylene chloride, ethylene chloride, chloroform and tetrachloroethylene, aromatic hydrocarbons, such as benzene, toluene, the xylenes and their isomer mixtures and gasoline, ethers, such as diethyl ether, di-n-butyl ether, methyl tert-butyl ether, tetrahydrofuran and dioxane, ketones, such as acetone, methyl ethyl ketone and methyl isopropyl ketone, and aprotic dipolar solvents, such as dimethylformamide, dimethyl sulfoxide or pyridine. Mixtures of these substances may also be used as solvents and diluents.

In every case, Y is a conventional leaving group, for example a sulfonic acid radical or a halogen. Among the sulfonic acid radicals, methanesulfonyl, trifluoromethanesulfonyl and p-toluenesulfonyl are preferred, where preferred halogens are chlorine and bromine, chlorine being particularly preferred.

For the preparation of the novel compounds Ia and Ib by the methods described above, starting materials are usually employed in a stoichiometric ratio. An excess of one or other of the starting materials may be quite advantageous in some specific cases.

The reactions usually take place at a sufficient rate at above $-20°$ C. In general, $120°$ C. need not be exceeded. Since in some cases the reactions take place with evolution of heat, it may be advantageous to provide a means of cooling.

The reaction mixtures are worked up in a conventional manner, for example by adding water, separating the phases and carrying out column chromatography. Some of the novel compounds of the formulae Ia and Ib are obtained in the form of colorless or pale brown, viscous oils, which can be freed from the final volatile constituents by prolonged heating to moderately elevated temperatures under reduced pressure (incipient distillation) and can be purified in this manner. If the compounds of the formulae Ia and Ib are obtained in crystalline form, they can be purified by recrystallization.

The substituents in formula I have the following specific meanings: $R^1$ is straight-chain or branched $C_1$–$C_{12}$-alkyl, preferably $C_1$–$C_8$-alkyl, particularly preferably branched $C_3$–$C_8$-alkyl, such as isopropyl, isobutyl, sec-butyl, tert-butyl, isopentyl, 1-methylbutyl, isohexyl, 1-methylpentyl, isoheptyl, 1-methylhexyl, 1-methylheptyl, 1,3-dimethylbutyl, 1,2-dimethylbutyl, 3-methylpentyl, 4-methylbutyl, 1-ethylpropyl or 1-ethylbutyl; straight-chain or branched $C_2$–$C_{12}$-alkenyl, preferably $C_2$–$C_8$-alkenyl, particularly preferably $C_3$–$C_6$-alkenyl, such as allyl, 1-methylallyl, 1,3-dimethylbut-2-enyl, 1-methylbut-2-enyl or but-3-en-1-yl; straight-chain or branched $C_2$–$C_{12}$-alkynyl, preferably $C_2$–$C_8$-alkynyl, particularly preferably $C_2$–$C_4$-alkynyl, such as ethynyl, propynyl, prop-2-ynyl, 1-methylprop-2-ynyl, but-2-ynyl or but-3-ynyl; straight-chain or branched $C_1$–$C_{12}$-haloalkyl, preferably $C_1$–$C_4$-haloalkyl, particularly preferably $C_1$–$C_4$-fluoro- or chloroalkyl, such as trifluoromethyl, difluoromethyl, fluoromethyl, trichloromethyl, pentfluoroethyl, 2,2,2-trifluoroethyl, 2,2,2-trichloroethyl, 1-fluoromethyl-2-fluoroethyl or 1-chloromethyl-2-chloroethyl; straight-chain or branched $C_2$–$C_{12}$-haloalkenyl, preferably $C_2$–$C_4$-haloalkenyl, particularly preferably $C_2$–$C_4$-fluoro- or chloroalkenyl, such as 1,2,2-trifluoroethenyl, 1,2,2-trichloroethenyl, 3,3-difluoroprop-2-enyl or 3,3-dichloroprop-2-enyl; straight-chain or branched $C_3$–$C_{12}$-alkoxyalkyl, preferably $C_3$–$C_9$-alkoxyalkyl, particularly preferably $C_1$–$C_4$-alkoxy-substituted $C_1$–$C_5$-alkoxyalkyl, for example 2-methoxyethyl, 2-methoxypropyl, 3-methoxyprop-2-yl, 3-methoxybutyl, 4-methoxybut-2-yl, 4-methoxybut-3-yl, 5-methoxypent-3-yl, 2-ethoxyethyl, 2-ethoxypropyl, 3-ethoxypropyl, 3-ethoxybutyl, 3-ethoxybut-2-yl, 5-ethoxypent-2-yl, 2-propoxyethyl, 2-propoxypropyl, 3-propoxybutyl, butoxymethyl or 2-butoxyprop-2-yl; $C_3$–$C_8$-cycloalkyl, preferably $C_3$–$C_6$-cycloalkyl, such as cyclopropyl, cyclobutyl, cyclopentyl or cyclohexyl; $C_4$–$C_{12}$-cycloalkylalkyl, preferably $C_4$–$C_8$-cycloalkylalkyl, such as cyclopropylmethyl, cyclopropylethyl, cyclobutylmethyl, cyclopentylmethyl, cyclohexylmethyl or cyclohexylethyl; $C_3$–$C_8$-halocycloalkyl, preferably $C_3$–$C_6$-halocycloalkyl, particularly preferably $C_3$–$C_6$-fluoro- or chlorocycloalkyl, such as 2,2-difluorocyclopropyl or 2,2-dichlorocyclopropyl; $C_4$–$C_{12}$-halocycloalkylalkyl, preferably $C_4$–$C_8$-halocycloalkylalkyl, particularly preferably $C_4$–$C_8$-fluoro- or chlorocycloalkylalkyl, such as 2,2-difluorocycloprop-1-ylmethyl or 2,2-dichlorocycloprop-1-ylmethyl; $C_4$–$C_{12}$-cycloalkylhaloalkyl, preferably $C_4$–$C_8$-cycloalkylhaloalkyl, particularly preferably $C_4$–$C_8$-cycloalkylfluoro- or -chloroalkyl, such as 2-cyclopropyl-2-chloroethyl or 2-cyclopropyl-1,1-difluoroethyl, or $C_4$–$C_{12}$-halocycloalkylhaloalkyl, preferably $C_4$–$C_8$-halocycloalkylhaloalkyl, particularly preferably $C_4$–$C_8$-fluoro- or chlorocycloalkylfluoro- or chloroalkyl, such as 2,2-dichlorocycloprop-1-yl-2-chloroethyl.

X is O, S or $SO_2$, preferably O or S, particularly preferably O.

In the case of $Q_a$, Z is hydrogen; halogen, preferably fluorine or chlorine; straight-chain or branched $C_1$–$C_8$-alkyl, preferably straight-chain or branched $C_1$–$C_4$-alkyl, such as methyl, ethyl, propyl, isopropyl, butyl or isobutyl, particularly preferably $C_1$- or $C_2$-alkyl, such as methyl or ethyl; straight-chain or branched $C_1$–$C_8$-alkoxy, preferably straight-chain or branched $C_1$–$C_4$-alkoxy, such as methoxy, ethoxy, propoxy, isopropoxy or butoxy, particularly preferably $C_1$- or $C_2$-alkoxy, such as methoxy or ethoxy; straight-chain or branched $C_1$–$C_4$-haloalkyl, preferably $C_1$- or $C_2$-fluoro or chloroalkyl, particularly preferably trifluoromethyl or trichloromethyl; straight-chain or branched $C_1$–$C_4$-haloalkoxy, preferably $C_1$- or $C_2$-fluoro- or chloroalkoxy, particularly preferably trifluoromethoxy or trichloromethoxy; $C_3$–$C_{10}$-cycloalkyl, preferably $C_3$–$C_6$-cycloalkyl, such as cyclopropyl, cyclobutyl, cyclopentyl or cyclohexyl, particularly preferably cyclopropyl; nitro or cyano; in the case of $Q_b$, Z is hydrogen or halogen, preferably fluorine, chlorine or straight-chain or branched $C_1$–$C_8$-alkoxy, particularly preferably phenyl which is monosubstituted by $C_1$- or $C_2$-alkoxy, such as 4-methoxyphenyl or 4-ethoxyphenyl; aryl which is monosubstituted to trisubstituted by straight-chain or branched $C_1$–$C_4$-haloalkyl, preferably phenyl which is monosubstituted by $C_1$- or $C_2$-fluoro- or chloroalkyl, particularly preferably phenyl which is monosubstituted by trifluoromethyl or trichloromethyl, such as 4-trifluoromethylphenyl or 4-trichloromethylphenyl; aryl which is monosubstituted to trisubstituted by straight-chain or branched $C_1$–$C_4$-haloalkoxy, preferably phenyl which is monosubstituted by $C_1$- or $C_2$-fluoro- or chloroalkoxy, particularly preferably phenyl which is monosubstituted by trifluoromethoxy or trichloromethoxy, such as 4-trifluoromethoxyphenyl or 4-trichloromethoxyphenyl, and $Q_b$ is an unsubstituted or substituted heteroaromatic having a 5-membered ring and from 1 to 4, in particular 1 or 2, heteroatoms, such as nitrogen, sulfur or oxygen, preferably thien-2-yl, thien-3yl, thiazol-5-yl, thiazol-4-yl, thiazol-2-yl, oxazol-5-yl, oxazol-4-yl, oxazol-2-yl, imidazol-5-yl, imidazol-4-yl, imidazol-2-yl, isothiazol-5-yl, isothiazol-3-yl, pyrazol-3-yl, pyrazol-4-yl, pyrazol-5-yl, isoxazol-5-yl, isoxazol-3-yl, 1,3,4-thiadiazol-2-yl, 1,3,4-oxadiazol-2-yl, 1,2,4-oxadiazol-3-yl, 1,3,4-triazol-2-yl or 1,2,4-thiadiazol-3-yl, particularly preferably thiophen-2-yl, thiophen-3-yl, thiazol-4-yl, imidazol-5-yl, pyrazol-3-yl, 1,3,4-thiadiazol-2-yl, 1,3,4-oxadiazol-2-yl, 1,2,4-oxadiazol-3-yl, isoxazol-5-yl or isoxazol-3-yl.

The hetaryl radical having a five-membered ring may be unsubstituted or monosubstituted or polysubstituted by: halogen, preferably fluorine, chlorine or bromine, particularly preferably chlorine or bromine, $C_1$–$C_8$-alkyl, preferably $C_1$–$C_4$-alkyl, particularly preferably methyl, ethyl, isopropyl or tert-butyl, $C_2$-$C_8$-alkenyl, preferably $C_2$-$C_4$-alkenyl, particularly preferably ethenyl, 1-methylethenyl, propenyl or 2-methylpropenyl, $C_1$-$C_4$-haloalkyl, preferably $C_1$- or $C_2$-haloalky which is substituted by fluorine or chlorine, particularly preferably trifluoromethyl or 2,2,2-trifluoroeth-1-yl, $C_1$-$C_8$-alkoxy, preferably $C_1$-$C_3$-alkoxy, particularly preferably methoxy, ethoxy, n-propoxy or isopropoxy, $C_1$-$C_8$-alkylthio, preferably $C_1$-$C_3$-alkylthio, particularly preferably methylthio, ethylthio, n-propylthio or isopropylthio, $C_2$-$C_8$-alkoxyalkyl, preferably $C_2$-$C_4$-alkoxyalkyl, particularly preferably methoxymethyl, 1-methoxyethyl, 2-methoxyethyl or 1-methoxypropyl, or $C_3$-$C_8$-cycloalkyl, preferably $C_3$-$C_5$-cycloalkyl, such as cyclopropyl, cyclobutyl or cyclopentyl.

The novel compounds Ia and Ib may contain one or more centers of asymmetry in the substituent $R^1$. The present invention embraces all possible stereoisomers, such as diastereomers, enantiomers, diastereomer mixtures and enantiomer mixtures. The compounds relating to the example compounds in the Table are the racemic mixture in each case. The phenoxyalkyl-substituted aromatics of the formula Ia and Ib are suitable for effectively combating pests from the class of insects, mites and nematodes. They may be used as pesticides in crop protection, and in the hygiene, stores protection and veterinary sectors.

Examples of injurious insects from the Lepidoptera order are *Plutella maculipennis, Leucoptera coffeella, Hyponomeuta malinellus, Argyresthia conjugella, Sitotroga cerealella, Phthorimaea operculella, Capua reticulana, Sparganothis pilleriana, Cacoecia murinana, Tortrix viridana, Clysia ambiguella, Evetria buoliana, Polychrosis botrana, Cydia pomonella, Laspeyresia molesta, Laspeyresia funebra, Ostrinia nubilalis, Loxostege sticticalis, Ephestia kuehniella, Chilo suppressalis, Galleria mellonella, Malacosoma neustria, Dendrolimus pini, Thaumatopoea pityocampa, Phalera bucephela, Cheimatobia brumata, Hibernia defoliaria, Bupalus pinarius, Hyphantria cunea, Agrotis segetum, Agrotis ypsilon, Barathra brassicae, Cirphis unipuncta, Prodenia litura, Laphygma exigua, Panolis flammea, Earis insulana, Plusia gamma, Alabama argillacea, Lymantria dispar, Lymantria monacha, Pieris brassicae,* and *Aporia crataegi;* examples from the Coleoptera order are Blitophaga undata, *Melanotus communis, Limonius californicus, Agriotes lineatus, Agriotes obscurus, Agrilus sinuatus, Meligethes aeneus, Atomaria linearis, Epilachna varicestris, Phyllopertha horticola, Popillia japonica, Melolontha melolontha, Melolontha hippocastani, Amphimallus solstitialis, Crioceris asparagi, Lema melanopus, Leptinotarsa decemlineata, Phaedon cochleariae, Phyllotreta nemorum, Chaetocnema tibialis, Phylloides chrysocephala, Diabrotica 12-punctata, Cassida nebulosa, Bruchus lentis, Bruchus rufimanus, Bruchus pisorum, Sitona lineatus, Otiorrhynchus sulcatus, Otiorrhynchus ovatus, Hylobies abietis, Byctiscus betulae, Anthonomus pomorum, Anthonomus grandis, Ceuthorrhynchus assimilis, Ceuthorrhynchus napi, Sitophilus granaria, Anisandrus dispar, Ips typographus,* and *Blastophagus piniperda;* examples from the Diptera order are *Lycoria pectoralis, Mayetiola destructor, Dasyneura brassicae, Contarinia tritici, Haplodiplosis equestris, Tipula paludosa, Tipula oleracea, Dacus cucurbitae, Dacus oleae, Ceratitis capitata, Rhagoletis cerasi, Rhagoletis pomonella, Anastrepha ludens, Oscinella frit, Phorbia coarctata, Phorbia antiqua, Phorbia brassicae, Pegomya hyoscyami, Anopheles maculipennis, Culex, pipiens, Aedes aegypti, Aedes vexans, Tabanus bovinus, Tipula paludosa, Musca domestica, Fannia canicularis, Muscina stabulans, Glossina morsitans, Oestrus ovis, Chrysomya macellaria, Chrysomya hominivorax, Lucilia cuprina, Lucilia sericata,* and *Hypoderma lineata;* examples from the Hymenoptera order are *Athalia rosae, Hoplocampa minuta, Monomorium pharaonis, Solenopsis geminata,* and *Atta sexdens;* examples from the Heteroptera order are *Nezara viridula, Eurygaster integriceps, Blissus leucopterus, Dysdercus cingulatus, Dysdercus intermedius, Piesma quadrata,* and *Lygus pratensis;* examples from the Homoptera order are *Perkinsiella saccharicida, Nilaparvata lugens, Empoasca fabae, Psylla mali, Psylla piri, Trialeurodes vaporariorum, Aphis fabae, Aphis pomi, Aphis sambuci, Aphidula nasturtii, Cerosipha gossypii, Sappaphis mali, Sappaphis mala, Dysaphis radicola, Brachycaudus cardui, Brevicoryne brassicae, Phorodon humuli, Rhopalomyzus ascalonicus, Myzodes persicae, Myzus cerasi, Dysaulacorthum pseudosolani, Acyrthosiphon onobrychis, Macrosiphon rosae, Megoura viciae, Schizoneura lanuginosa, Pemphigus bursarius, Dreyfusia nordmannianae, Dreyfusia piceae, Adelges laricis,* and *Viteus vitifolii;* examples from the Isoptera order are Reticulitermes lucifugus, *Calotermes flavicollis, Leucotermes flavipes,* and *Termes natalensis;* examples from the Orthoptera order are *Forficula auricularia, Acheta domestica, Gryllotalpa gryllotalpa, Tachycines asynamorus, Locusta migratoria, Staunonotus maroccanus, Schistocerca peregrina, Nomadacris septemfasciata, Melanoplus spretus, Melanoplus femur-rubrum, Blatta orientalis, Blattella germanica, Periplaneta americana,* and *Blabera gigantea.*

Examples of mites and ticks (Acarina) belonging to the Arachnida class are *Tetranychus telarius, Tetranychus pacificus, Paratetranychus pilosus, Bryobia praetiosa, Ixodes ricinus, Ornithodorus moubata, Amblyomma americanum, Dermacentor silvarum,* and *Boophilus microplus.*

Examples from the Nemathelminthes class are root-knot nematodes, e.g., *Meloidogyne incognita, Meloidogyne hapla* and *Meloidogyne javanica,* cyst-forming nematodes, e.g., *Heterodera rostochiensis, Heterodera schachtii, Heterodera avenae, Heterodera glycines,* and *Heterodera trifolii,* and stem and leaf eelworms, e.g., *Ditylenchus dipsaci, Ditylenchus destructor, Pratylenchus neglectus, Pratylenchus penetrans, Pratylenchus goodeyi, Pratylenchus curvitatus* and *Tylenchorhynchus dubius, Tylenchorhynchus claytoni, Rotylenchus robustus, Heliocotylenchus multicinctus, Radopholus similis, Belonolaimus longicaudatus, Longidorus elongatus,* and *Trichodorus primitivus.*

The active ingredients may be applied for instance as such, or in the form of formulations or application forms prepared therefrom, e.g., directly sprayable solutions, powders, suspensions, dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the active ingredients according to the invention as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose. Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations generally contain from 0.1 to 95, and preferably 0.5 to 90, % by weight of active ingredient.

Examples of formulations are given below.

I. 5 parts by weight of compound no. A1 is intimately mixed with 95 parts by weight of particulate kaolin. A dust is obtained containing 5% by weight of the active ingredient.

II. 30 parts by weight of compound no. A4 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

III. 10 parts by weight of compound no. A50 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

IV. 20 parts by weight of compound no. B1 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

V. 80 parts by weight of compound no. B10 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

The active ingredient concentrations in the finished formulations may vary over a wide range. Generally, they are from 0.0001 to 10, and preferably from 0.01 to 1, %. The active ingredients may also successfully be used in the ultra-low-volume (ULV) method, where it is possible to apply formulations containing more than 95 wt % of active ingredient, or even the active ingredient without additives.

In the open, the amount of active ingredients applied is for example from 0.001 to 2, particularly from 0.01 to 1, kg/ha.

There may be added to the active ingredients (if desired, immediately before use (tankmix)) oils of various types, herbicides, fungicides, other pesticides and bactericides. These agents may be added to the active ingredients according to the invention in a weight ratio of from 1:10 to 10:1.

MANUFACTURING EXAMPLES

A) N-Phenoxymethyl-substituted azoles ($Q_a$)

1-[4-(1-Methyl-1-propyloxy)-phenoxymethyl]-4,5-dichloroimidazole (Compound no. A4)

Under a nitrogen blanket and at room temperature (about 20° C.), 5.0 g of 4-(1-methyl-1-propyloxy)-phenol in 20 ml of anhydrous dimethylformamide is dripped into 0.79 g of 80% strength sodium hydride in 50 ml of anhydrous dimethylformamide. After the exothermic reaction has subsided (evolution of hydrogen), the mixture is stirred for a further 30 minutes at 60° C. Subsequently, 6.12 g of 1-chloromethyl-4,5-dichloroimidazole in 20 ml of anhydrous dimethylformamide is dripped in at room temperature. The whole is poured into 150 ml of ice water, followed by extraction three times with ethyl acetate. The organic phases are washed with 5% strength sodium hydroxide solution and with water. Drying over sodium sulfate and concentration under reduced pressure gives a crude product which is purified by chromatography on silica gel using toluene/ethyl acetate (9:1) as eluant. There is obtained 4.3 g of 1-[4-(1-methyl-1-propyloxy)-phenoxymethyl]-4,5-dichloroimidazole; $n_D^{22} = 1.5475$.

1-[4-(3,3-Dimethyl-1-propyloxy)-phenoxymethyl]-4,5-dichloroimidazole (Compound no. A50)

Under a nitrogen blanket and at room temperature, 5.8 g of 4-(3,3-dimethyl-1-proplyoxy)-phenol in 20 ml of anhydrous dimethylformamide is dripped into 0.79 g of 80% strength sodium hydride in 50 ml of anhydrous dimethylformamide. After hydrogen evolution has subsided, the mixture is stirred for a further hour at 60° C. Subsequently, 6.12 g of 1-chloromethyl-4,5-dichloroimidazole in 20 ml of anhydrous dimethylformamide is dripped in at room temperature. The whole is then stirred for 3 hours at 80° C. and overnight at room temperature. The mixture is then poured into 100 ml of ice water, followed by extraction three times with methyl tert-butyl ether. The organic phases are washed with 5% strength sodium hydroxide solution and three times with water, dried over sodium sulfate and concentrated under reduced pressure. The residue is recrystallized from cyclohexane. There is obtained 7.4 g of 1-[4-(3,3-dimethyl-1-propyloxy)-phenoxymethyl]-4,5-dichloroimidazole having a melting point of 105°–108° C.

Compounds Iaa to Iaf listed in Tables 1 to 6 below may be obtained in accordance with these directions.

Compounds Iaa to Iaf without any physical data in Tables 1 to 6 may be readily obtained from appropriate starting materials; they are expected to have a similar action.

TABLE 1

(Iaa)

$R^1-X-\underset{Z}{\text{C}_6H_3}-OCH_2-N\underset{R^5\;\;R^4}{\overset{R^3}{\underset{\Vert}{\text{C}=N}}}$

| No. | $R^1$ | Z | $R^3$ | $R^4=R^5$ | X | Phys. data |
|---|---|---|---|---|---|---|
| A1 | (CH₃)₂CH— | H | H | Cl | O | $n_D^{24}$: 1.5421 |
| A2 | (CH₃)₂CH— | H | H | Cl | S | |
| A3 | (CH₃)₂CH— | H | H | Cl | SO₂ | |
| A4 | CH₃CH₂CH(CH₃)— | H | H | Cl | O | $n_D^{23}$: 1.5475 |
| A5 | CH₃CH₂CH(CH₃)— | H | H | Cl | S | $n_D^{24}$: 1.5795 |
| A6 | CH₂CH₂CH(CH₃)— | H | H | Cl | SO₂ | mp: 111–114° C. |
| A7 | CH₃CH₂CH(CH₃)— | 3-F | H | Cl | O | |
| A8 | CH₃CH₂CH(CH₃)— | 3-F | H | Cl | S | |
| A9 | CH₃CH₂CH(CH₃)— | 3-F | H | Cl | SO₂ | |
| A10 | CH₃CH₂CH(CH₃)— | 3-Cl | H | Cl | O | |
| A11 | CH₃CH₂CH(CH₃)— | 3-Cl | H | Cl | S | |
| A12 | CH₃(CH₂)₂CH(CH₃)— | H | H | Cl | O | |
| A13 | CH₃(CH₂)₂CH(CH₃)— | H | H | Cl | S | |
| A14 | CH₃(CH₂)₃CH(CH₃)— | H | H | Cl | O | |
| A15 | CH₃(CH₂)₃CH(CH₃)— | H | H | Cl | S | |
| A16 | CH₃(CH₂)₄CH(CH₃)— | H | H | Cl | O | |
| A17 | CH₃(CH₂)₄CH(CH₃)— | H | H | Cl | S | |

TABLE 1-continued (Iaa)

$$R^1-X-\underset{Z}{\underset{|}{\bigcirc}}-OCH_2-N\underset{R^5}{\overset{R^3}{\underset{|}{\diagdown}}}\underset{R^4}{\overset{N}{\diagup}}$$

| No. | R¹ | Z | R³ | R⁴=R⁵ | X | Phys. data |
|---|---|---|---|---|---|---|
| A18 | CH₃(CH₂)₅CH(CH₃)— | H | H | Cl | O | |
| A19 | CH₃(CH₂)₅CH(CH₃)— | H | H | Cl | S | |
| A20 | (CH₃)₂CHCH₂CH(CH₃)— | H | H | Cl | O | $n_D^{23}$: 1.5373 |
| A21 | (CH₃)₂CHCH₂CH(CH₃)— | H | H | Cl | S | |
| A22 | C₂H₅(CH₃)CH—CH(CH₃)— | H | H | Cl | O | |
| A23 | C₂H₅(CH₃)CH—CH(CH₃)— | H | H | Cl | S | |
| A24 | H₂C=CH—CH(CH₃)— | H | H | Cl | O | |
| A25 | CH₂=CH—CH(CH₃)— | H | H | Cl | S | |
| A26 | CH₂=CH—CH(CH₃)— | H | H | Cl | SO₂ | |
| A27 | CH₂=CH—CH₂— | H | H | Cl | O | |
| A28 | CH₂=CH—CH₂— | H | H | Cl | S | |
| A29 | Cl₂C=CH—CH₂— | H | H | Cl | O | |
| A30 | Cl₂C=CH—CH₂— | H | H | Cl | S | |
| A31 | (CH₃)₂C=CH—CH₂— | H | H | Cl | O | |
| A32 | (CH₃)₂C=CH—CH₂— | H | H | Cl | S | |
| A33 | Cyclobutyl | H | H | Cl | O | |
| A34 | Cyclobutyl | H | H | Cl | S | |
| A34 | Cyclopentyl | H | H | Cl | O | |
| A35 | cyclopentyl | H | H | Cl | S | |
| A36 | cyclohexyl | H | H | Cl | O | |
| A37 | cyclohexyl | H | H | Cl | S | |

TABLE 1-continued (Iaa)

$$R^1-X-\text{C}_6H_3(Z)-OCH_2-N(-C(R^3)=N-)=C(R^5)(R^4)$$

| No. | R¹ | Z | R³ | R⁴=R⁵ | X | Phys. data |
|-----|-----|---|-----|-------|-----|-----------|
| A38 | cyclopropyl-methyl | H | H | Cl | O | |
| A39 | cyclohexyl-methyl | H | H | Cl | O | |
| A40 | Cl₂C(CH₂—CHCH₂—) | H | H | Cl | O | mp.: 94–96° C. |
| A41 | Cl₂C(CH₂—CHCH₂—) | H | H | Cl | S | |
| A42 | Cl₂C(CH₂—CHCH₂—) | H | H | Cl | SO₂ | |
| A43 | Cl₂C(CH₂—CHCH₂—) | 3-F | H | Cl | O | |
| A44 | HC≡C—CH₂— | H | H | Cl | O | |
| A45 | ClC≡C—CH₂— | H | H | Cl | O | |
| A46 | HC≡C—CH(CH₃)— | H | H | Cl | O | |
| A47 | (CH₃)₂C=CH—CH(CH₃)— | H | H | Cl | O | |
| A48 | (CH₃)₂CHCH₂— | H | H | Cl | O | mp.: 65–68° C. |
| A49 | (CH₃)₂CH(CH₂)₂— | H | H | Cl | O | |
| A50 | (CH₃)₂CHCH₂— | H | H | Cl | S | |
| A51 | (C₂H₅)₂CH— | H | H | Cl | O | $n_D^{22}$: 1.5475 |
| A52 | (CH₂F)₂CH— | H | H | Cl | O | |
| A53 | CF₃CH₂— | H | H | Cl | O | |
| A54 | Cl₂C(CH₂—CH—CH(CH₃)—) | H | H | Cl | O | |
| A55 | ClCH=CHCH₂— | H | H | Cl | O | |
| A56 | (CH₃)₃CCH₂— | H | H | Cl | O | mp.: 105–108° C. |
| A57 | CH₃CH₂CH₂— | H | H | Cl | O | |
| A58 | CH₃CH₂CH₂CH₂— | H | H | Cl | O | |
| A59 | CH₃— | H | H | Cl | O | |
| A60 | CH₃CH₂— | H | H | Cl | O | |
| A61 | CH₃(CH₂)₂CH₂— | H | H | Cl | S | |
| A62 | (CH₃)₃C(CH₂)₂— | H | H | Cl | O | |
| A63 | (CH₃)₃CCH₂CH(CH₃)— | H | H | Cl | O | |
| A64 | CH₃CH₂CH(CH₃)—CH₂— | H | H | Cl | O | |
| A65 | CH₃(CH₂)₂—CH(C₂H₅)— | H | H | Cl | O | $n_D^{22}$: 1.5365 |

TABLE 1-continued (Iaa)

R¹—X—[phenyl with Z]—OCH₂—N(R³)=N—C(R⁴)=C(R⁵) [imidazole ring]

| No. | R¹ | Z | R³ | R⁴=R⁵ | X | Phys. data |
|---|---|---|---|---|---|---|
| A66 | (CH₃)₂CH—CH(CH₃)— | H | H | Cl | O | $n_D^{22}$: 1.5421 |
| A67 | (CH₃)₂CH—CH(CH₃)— | H | H | Cl | O | |
| A68 | (CH₃)₂C=CH—CH₂— | H | H | Cl | O | |
| A69 | CH₃CH(CH₃)— with F | H | H | Cl | O | |
| A70 | ClCH₂CH(CH₃)— | H | H | Cl | O | |
| A71 | Cl(CH₂)₂CH(CH₃)— | H | H | Cl | O | |
| A72 | CH₃OCH(CH₃)CH₂— | H | H | Cl | O | |
| A73 | CH₃OCH(CH₃)—(CH₂)₂— | H | H | Cl | O | |
| A74 | CH₃OCH₂—CH(CH₃) | H | H | Cl | O | $n_D^{22}$: 1.5500 |
| A75 | CH₃CH₂O(CH₂)₂— | H | H | Cl | O | $n_D^{22}$: 1.5500 |
| A76 | CH₃O(CH₂)₂CH(CH₃)— | H | H | Cl | O | |
| A77 | CH₃O(CH₂)₂— | H | H | Cl | O | $n_D^{22}$: 1.5575 |
| A78 | CH₃OCH₂CH(CH₃)— | H | H | Cl | S | |
| A79 | CH₃CH₂CH(CH₃)— | H | H | H | O | |
| A80 | CH₃CH₂CH(CH₃)— | H | H | H | S | |
| A81 | CH₃CH₂CH(CH₃)— | H | H | H | SO₂ | |
| A82 | (CH₃)₂CH— | H | H | H | O | |
| AA3 | CCl₂(CH₂—CH—CH₂—) | H | H | H | O | |
| A84 | CH₃O(CH₂)₂— | H | H | H | O | |

TABLE 1-continued (Iaa)

R¹—X—[phenyl(Z)]—OCH₂—N(—C(R³)=N)—C(R⁵)=C(R⁴)

| No. | R¹ | Z | R³ | R⁴=R⁵ | X | Phys. data |
|---|---|---|---|---|---|---|
| A85 | CH$_3$OCH$_2$CH(CH$_3$)— | H | H | H | O | |
| A86 | (CH$_3$)$_2$CHCH$_2$CH(CH$_3$)— | H | H | H | O | |
| A87 | (CH$_3$)$_2$CHCH$_2$CH(CH$_3$)— | H | H | CH$_3$ | O | |
| A88 | CH$_3$OCH$_2$CH(CH$_3$)— | H | H | CH$_3$ | O | |
| A89 | CH$_3$O(CH$_2$)$_2$— | H | H | CH$_3$ | O | |
| A90 | (CH$_3$)$_2$CH— | H | H | CH$_3$ | O | |
| A91 | Cl$_2$C(CH$_2$CHCH$_2$—)  [2,2-dichlorocyclopropylmethyl] | H | H | CH$_3$ | O | |
| A92 | CH$_3$CH$_2$CH(CH$_3$)— | H | H | CH$_3$ | O | |
| A93 | CH$_3$CH$_2$CH(CH$_3$)— | H | H | CH$_3$ | S | |
| A94 | CH$_3$CH$_2$CH(CH$_3$)— | H | H | CH$_3$ | SO$_2$ | |

TABLE 2

(Iab)

R¹—X—[phenyl(Z)]—OCH₂—N=C(R⁶)—C(R⁸)=C(R⁷)...

| No. | R¹ | Z | R⁶ | R⁷ | R⁸ | X | Phys. data |
|---|---|---|---|---|---|---|---|
| A95 | (CH$_3$)$_2$CH— | H | H | H | H | O | |
| A96 | (CH$_3$)$_2$CH— | H | H | H | H | S | |
| A97 | CH$_3$CH$_2$CH(CH$_3$)— | H | H | H | H | O | |
| A98 | CH$_3$CH$_2$CH(CH$_3$)— | H | H | H | H | S | |
| A99 | CH$_3$CH$_2$CH(CH$_3$)— | H | H | H | H | SO$_2$ | |
| A100 | CH$_3$OCH$_2$CH$_2$— | H | H | H | H | O | |
| A101 | CH$_3$OCH$_2$CH$_2$— | H | H | H | H | S | |
| A102 | CH$_3$OCH$_2$CH(CH$_3$)— | H | H | H | H | O | |
| A103 | CH$_3$OCH$_2$CH(CH$_3$)— | H | H | H | H | S | |
| A104 | (CH$_3$)$_2$CHCH$_2$CH(CH$_3$)— | H | H | H | H | O | |
| A105 | (CH$_3$)$_2$CHCH$_2$CH(CH$_3$)— | H | H | H | H | S | |
| A106 | Cl$_2$C(CH$_2$CHCH$_2$—)  [2,2-dichlorocyclopropylmethyl] | H | H | H | H | O | |

TABLE 2-continued (Iab)

Structure: R¹—X—[phenyl with Z]—OCH₂—N(—N=CR⁶—CR⁸=CR⁷—)

| No. | R¹ | Z | R⁶ | R⁷ | R⁸ | X | Phys. data |
|---|---|---|---|---|---|---|---|
| A107 | Cl₂C(CH₂—CH—CH₂—) | H | H | H | H | S | |
| A108 | Cl₂C(CH₂—CH—CH₂—) | H | H | H | H | SO₂ | |

TABLE 3

(Iac)

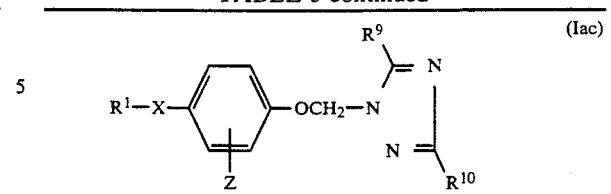

| No. | R¹ | Z | R⁹=R¹⁰ | X | Phys. data |
|---|---|---|---|---|---|
| A109 | CH₃CH₂CH(CH₃)— | H | H | O | $n_D^{21}$: 1.5310 |
| A110 | CH₃CH₂CH(CH₃)— | H | H | S | $n_D^{21}$: 1.5665 |
| A111 | CH₃CH₂CH(CH₃)— | H | H | SO₂ | |
| A112 | Cl₂C(CH₂—CH—CH₂—) | H | H | O | $n_D^{21}$: 1.5635 |
| A113 | Cl₂C(CH₂—CH—CH₂—) | H | H | S | |
| A114 | (CH₃)₂CH— | H | H | O | $n_D^{21}$: 1.5360 |
| A115 | (CH₃)₂CH— | H | H | S | |
| A116 | CH₃O(CH₂)₂— | H | H | O | |
| A117 | CH₃OCH₂CH(CH₃)— | H | H | O | |
| A118 | (CH₃)₂CHCH₂CH(CH₃)— | H | H | O | $n_D^{21}$: 1.5210 |
| A119 | (CH₃)₂CHCH₂CH(CH₃)— | H | CH₃ | O | |
| A120 | CH₃OCH₂CH(CH₃)— | H | CH₃ | O | |
| A121 | CH₃O(CH₂)₂— | H | CH₃ | O | |
| A122 | (CH₃)₂CH— | H | CH₃ | O | |

TABLE 3-continued (Iac)

| No. | R¹ | Z | R⁹=R¹⁰ | X | Phys. data |
|---|---|---|---|---|---|
| A123 | Cl₂C(CH₂—CH—CH₂—) | H | CH₃ | O | |
| A124 | CH₃CH₂CH(CH₃)— | H | CH₃ | SO₂ | |
| A125 | CH₃CH₂CH(CH₃)— | H | CH₃ | S | |
| A126 | CH₃CH₂CH(CH₃)— | H | CH₃ | O | |

TABLE 4

(Iad)

Structure: R¹—X—[phenyl with Z]—OCH₂—N(—N=CR¹¹—N=CR¹²—)

| No. | R¹ | Z | R¹¹ | R¹² | X | Phys. data |
|---|---|---|---|---|---|---|
| A127 | CH₃CH₂CH(CH₃)— | H | H | Cl | O | |
| A128 | CH₃CH₂CH(CH₃)— | H | H | Cl | S | |
| A129 | CH₃CH₂CH(CH₃)— | H | H | Cl | SO₂ | |
| A130 | Cl₂C(CH₂—CH—CH₂—) | H | H | Cl | O | |
| A131 | Cl₂C(CH₂—CH—CH₂—) | H | H | Cl | S | |
| A132 | (CH₃)₂CH— | H | H | Cl | O | |
| A133 | CH₃O(CH₂)₂— | H | H | Cl | O | |
| A134 | CH₃OCH₂CH(CH₃)— | H | H | Cl | O | |
| A135 | (CH₃)₂CHCH₂CH(CH₃)— | H | H | Cl | O | |
| A136 | (CH₃)₂CHCH₂CH(CH₃)— | H | H | H | O | |

TABLE 4-continued (Iad) structure: R¹—X—[phenyl with Z]—OCH₂—N(—C(R¹²)=N—N=C(R¹¹)—) cyclic

| No. | R¹ | Z | R¹¹ | R¹² | X | Phys. data |
|---|---|---|---|---|---|---|
| A137 | CH₃OCH₂CH(CH₃)— | H | H | H | O | |
| A138 | CH₃O(CH₂)₂— | H | H | H | O | |
| A139 | (CH₃)₂CH— | H | H | H | O | |
| A140 | Cl₂C(CH₂—CH—CH₂—) | H | H | H | O | |
| A141 | CH₃CH₂CH(CH₃)— | H | H | H | SO₂ | |
| A142 | CH₃CH₂CH(CH₃)— | H | H | H | S | |
| A143 | CH₃CH₂CH(CH₃)— | H | H | H | O | |

TABLE 5

(Iae) structure: R¹—X—[phenyl with Z]—OCH₂—N linked to indazole with R¹³

| No. | R¹ | Z | R¹³ | X | Phys. data |
|---|---|---|---|---|---|
| A144 | CH₃CH₂CH(CH₃)— | H | H | O | $n_D^{25}$: 1.5755 |
| A145 | CH₃CH₂CH(CH₃)— | H | H | S | |
| A146 | CH₃CH₂CH(CH₃)— | H | H | SO₂ | |
| A147 | Cl₂C(CH₂—CH—CH₂—) | H | H | O | |
| A148 | (CH₃)₂CH— | H | H | O | $n_D^{25}$: 1.5817 |
| A149 | CH₃O(CH₂)₂— | H | H | O | |
| A150 | CH₃OCH₂CH(CH₃)— | H | H | O | $n_D^{25}$: 1.5745 |
| A151 | (CH₃)₂CH₂CH(CH₃)— | H | H | O | |

TABLE 6

(Iaf) structure: R¹—X—[phenyl with Z]—OCH₂—N linked to benzimidazole with R¹⁴

| No. | R¹ | Z | R³ | R¹⁴ | X | Phys. data |
|---|---|---|---|---|---|---|
| A152 | CH₃CH₂CH(CH₃)— | H | H | H | O | |
| A153 | CH₃CH₂CH(CH₃)— | H | H | H | S | |
| A154 | CH₃CH₂CH(CH₃)— | H | H | H | SO₂ | |
| A155 | Cl₂C(CH₂—CH—CH₂—) | H | H | H | O | |
| A156 | (CH₃)₂CH— | H | H | H | O | |
| A157 | CH₃O(CH₂)₂— | H | H | H | O | |
| A158 | CH₃OCH₂CH(CH₃)— | H | H | H | O | |
| A159 | (CH₃)₂CHCH₂CH(CH₃)— | H | H | H | O | |
| A160 | (CH₃)₂CHCH₂CH(CH₃)— | H | H | CH₃ | O | |

B) Phenoxyalkyl-substituted heteroaromatics having a 5-membered ring ($Q_b$)

5-[4-(sec-Butoxy)-phenoxymethyl]-3-methylisoxazole (Ex. No. B1 in the table below):

4.6 g of anhydrous potassium carbonate is added to 5.0 g of 4-sec-butyloxyphenol in 80 ml of absolute dimethylformamide, and the mixture is stirred for one hour at 80° C. At this temperature, 3.9 g of 5-chloromethyl-3-methylisoxazole is dripped in and the mixture is stirred for a further seven hours at 90° C. The batch is then stirred into 300 ml of ice water, extracted three times, each time with 100 ml of methyl tert-butyl ether and the organic phase is washed twice with 2N sodium hydroxide solution (50 ml in each instance) and then three times with water (50 ml in each instance). Drying over sodium sulfate and removal of the solvent under reduced pressure give 6.6 g of 5-[4(sec-butyloxy)-phenoxymethyl]-3-methylisoxazole, which is obtained, after chromatography over silica gel using toluene-/ethyl acetate(1:1) as eluant, as a viscous oil. According to ¹H-NMR spectroscopy, the oil is pure.

250 MHz ¹H-NMR in CDCl₃ [ppm], (characteristic signals): 1.21 (d); 5.08 (s); 6.15 (s).

5-[4-(sec-Butylthio)-phenoxymethyl]-3-cyclopropylisoxazole (Ex. No. B10 in the table below):

Under a nitrogen blanket, 0.79 g of sodium hydride is added to 50 ml of absolute dimethylformamide. At room temperature, 5.5 g of 4-sec-butylthiophenol dissolved in 20 ml absolute dimethylformamide is dripped in and the mixture is stirred for 30 minutes at 60° C. At this temperature 5.8 g of 5-chloromethyl-3-cyclopropylisoxazole in 20 ml absolute dimethylformamide is dripped in and, after all has been added, the mixture is stirred for 3 hours at 90° C. Working up as in the above example gives, after chromatography over silica gel using toluene/ethyl acetate (1:1) as eluant, 7.9 g of 5-[4-(sec-butylthio)-phenoxymethyl]-3-cyclopropylisoxazole as a pale yellow oil.

250 MHz $^1$H-NMR in CDCl$_3$ [ppm]; (characteristic signals): 1.22 (d); 5.09 (s); 6.01 (s).

2-[4-(sec-Butyloxy)-phenoxymethyl]-5-bromothiophene (Ex. No. B49 in the table below):

6.64 g of 4-(sec-butyloxy)-phenol and 5.52 g of potassium carbonate are heated in 50 ml of anhydrous dimethylformamide for one hour at 70° C. Subsequently, 8.46 g of 5-bromo-2-chloromethylthiophene in 20 ml anhydrous dimethylformamide is dripped in. The mixture is stirred for 6 hours at 80° C. and overnight at room temperature (about 20° C.). It is then poured into 100 ml of ice water and extracted three times with ethyl acetate, and the organic phases are dried over magnesium sulfate. The solvent is evaporated off to give a crude product which is purified by chromatography on silica gel using n-hexane/ethyl acetate (4:1) as eluant. There is obtained 6.3 g of 2-[4-(sec-butyloxy)-phenoxymethyl]-5-bromothiophene as a colorless oil.

250 MHz $^1$H-NMR in CDCl$_3$ [ppm]; (characteristic signals): 0.99 (t); 1.28 (d); 5.09 (s).

5-[4-(sec-Butyloxy)-phenoxymethyl]-3-cyclopropyl-1,2,4-oxadiazole (Ex. No. B69 in the table below):

5 g of 4-(sec-butyloxy)-phenol and 6.2 g of potassium carbonate are stirred in 50 ml of anhydrous dimethylformamide for 1 hour at 80° C. Subsequently, 4.8 g of 5-chloromethyl-3-cyclopropyl-1,2,4-oxadiazole in 20 ml anhydrous dimethylformamide is dripped in and the mixture stirred for 8 hours at 80° C. and overnight at room temperature (about 20° C.). The mixture is then poured into 100 ml of water and extracted three times with ethyl acetate, and the organic phases are dried over magnesium sulfate. The solvent is evaporated off and the crude product is purified by chromatography on silica gel using n-hexane/ethyl acetate (4:1) as eluant. There is obtained 6.7 g of 5-[4-(sec-butyloxy)-phenoxymethyl]-3-cyclopropyl-1,2,4-oxadiazole as a colorless oil.

250 MHz $^1$H-NMR in CDCl$_3$ [ppm]; (characteristic signals): 1.50–1.82 (m); 2.04–2.18 (m); 5.13 (s).

TABLE 7

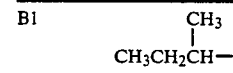

| No. | R$^1$ | R$^2$ | Z | X | Q$_b$ | Substitution in position ... of Q$_b$ | 250 MHz $^1$H-NMR [ppm] in CDCl$_3$ (characteristic signals) |
|---|---|---|---|---|---|---|---|
| B1 | CH$_3$CH$_2$CH(CH$_3$)— | H | H | O | 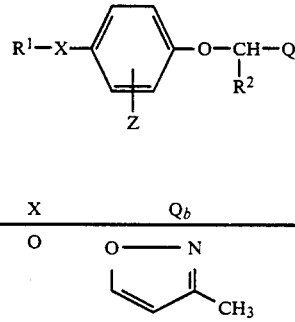 | 5 | 1.21 (d), 5.08 (s), 6.15 (s) |
| B2 | (CH$_3$)$_2$CHCH$_2$CH$_2$— | H | H | O | 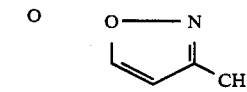 | 5 | 0.98 (d), 2.31 (s), 6.18 (s) |
| B3 | CH$_3$CH$_2$CH$_2$CH(CH$_3$)— | H | H | O | 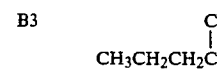 | 5 | 0.92 (t), 1.26 (d), 5.09 (s) |
| B4 | (CH$_3$)$_2$CHCH$_2$CH(CH$_3$)— | H | H | O | 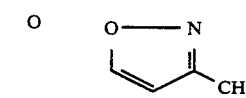 | 5 | 0.93 (t), 1.22 (d), 2.31 (s) |
| B5 | CH$_3$(CH$_2$)$_3$CH(CH$_3$)— | H | H | O | 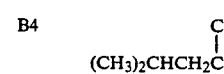 | 5 | 2.28 (s), 5.08 (s), 6.17 (s) |
| B6 | CH$_3$CH$_2$CH(CH$_3$)— | H | H | S | 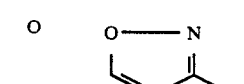 | 5 | 2.30 (s), 5.12 (s), 6.19 (s) |
| B7 | (CH$_3$)$_2$CH— | H | H | O | 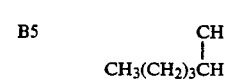 | 5 | 1.31 (d), 2.33 (s), 6.19 (s) |
| B8 | (CH$_3$)$_3$CCH$_2$CH$_2$— | H | H | O | 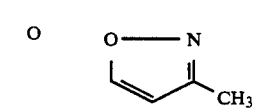 | 5 | 0.98 (s), 2.31 (s), 5.10 (s) |

TABLE 7-continued

R¹—X—⟨phenyl(Z)⟩—O—CH(R²)—Q_b

| No. | R¹ | R² | Z | X | Q_b | Substitution in position ... of Q_b | 250 MHz ¹H-NMR [ppm] in CDCl₃ (characteristic signals) |
|---|---|---|---|---|---|---|---|
| B9 | CH₃CH₂CH(CH₃)— | H | H | O | isoxazoline-cyclopropyl | 5 | 1.22 (d), 5.10 (s), 5.98 (s) |
| B10 | CH₃CH₂CH(CH₃)— | H | H | S | isoxazoline-cyclopropyl | 5 | 1.22 (d), 5.09 (s), 6.01 (s) |
| B11 | CH₃CH₂CH(CH₃)— | H | H | SO₂ | isoxazoline-cyclopropyl | 5 | 1.05 (t), 5.22 (s), 6.09 (s) |
| B12 | CH₃CH(F)CH(CH₃)— | H | H | O | isoxazoline-cyclopropyl | 5 | 1.32 (d), 4.21–4.83 (m), 5.02 (s) |
| B13 | (CH₃)₂CH— | H | H | O | isoxazoline-cyclopropyl | 5 | 1.35 (d), 5.08 (s), 6.89 (s) |
| B14 | CH₃OCH(CH₃)CH₂— | H | H | O | isoxazoline-cyclopropyl | 5 | 1.28 (d), 3.46 (s), 5.98 (s) |
| B15 | CH₃OCH₂CH₂— | H | H | O | isoxazoline-cyclopropyl | 5 | 3.42 (s), 3.63–3.71 (m), 3.91–4.05 (m) |
| B16 | (Cl₂C-CH₂-cyclopropyl)CH—CH₂— | H | H | O | isoxazoline-cyclopropyl | 5 | 4.08 (d), 5.05 (s), 6.00 (s) |
| B17 | (CH₃)₂CHCH₂CH(CH₃)— | H | H | O | isoxazoline-cyclopropyl | 5 | 1.23 (d), 4.98 (s), 5.96 (s) |
| B18 | (CH₃)₃CCH₂CH(CH₃)— | H | H | O | isoxazoline-cyclopropyl | 5 | |

TABLE 7-continued $$R^1-X-\underset{Z}{\underset{|}{C_6H_3}}-O-\underset{R^2}{\underset{|}{CH}}-Q_b$$

| No. | $R^1$ | $R^2$ | Z | X | $Q_b$ | Substitution in position ... of $Q_b$ | 250 MHz $^1$H-NMR [ppm] in CDCl$_3$ (characteristic signals) |
|---|---|---|---|---|---|---|---|
| B19 | CH$_3$OCH$_2$CH$_2$CH(CH$_3$)— | H | H | O | isoxazoline-cyclopropyl | 5 | 3.48 (s), 5.07 (s), 6.00 (s) |
| B20 | CH$_3$CH$_2$CH$_2$CH(CH$_3$)— | H | H | O | isoxazoline-cyclopropyl | 5 | |
| B21 | Cl$_2$C(CH$_2$)CH—CH$_2$— (dichlorocyclopropylmethyl) | H | H | S | isoxazoline-cyclopropyl | 5 | |
| B22 | CH$_3$OCH$_2$CH$_2$— | H | H | S | isoxazoline-cyclopropyl | 5 | |
| B23 | CH$_3$OCH$_2$CH(CH$_3$)— | H | H | S | isoxazoline-cyclopropyl | 5 | |
| B24 | C$_2$H$_5$OCH$_2$CH$_2$— | H | H | O | isoxazoline-cyclopropyl | 5 | |
| B25 | CH$_3$CH$_2$CH(CH$_3$)— | H | H | O | isoxazoline-cyclopropyl (3-pos) | 3 | |
| B26 | CH$_3$CH$_2$CH(CH$_3$)— | H | H | S | isoxazoline-cyclopropyl (3-pos) | 3 | |
| B27 | CH$_3$CH$_2$CH(CH$_3$)— | H | H | SO$_2$ | isoxazoline-cyclopropyl (3-pos) | 3 | |
| B28 | (CH$_3$)$_2$CH— | H | H | O | isoxazoline-cyclopropyl (3-pos) | 3 | |

TABLE 7-continued $$R^1-X-\underset{Z}{\underset{|}{\bigcirc}}-O-\underset{R^2}{\underset{|}{CH}}-Q_b$$

| No. | R$^1$ | R$^2$ | Z | X | Q$_b$ | Substitution in position ... of Q$_b$ | 250 MHz $^1$H-NMR [ppm] in CDCl$_3$ (characteristic signals) |
|---|---|---|---|---|---|---|---|
| A29 | CH$_3$OCH$_2$CH(CH$_3$)— | H | H | O | 3-(cyclopropyl)isoxazole | 3 | 1.27 (d), 3.40 (s), 5.18 (s) |
| A30 | CH$_3$OCH$_2$CH$_2$— | H | H | O | 3-(cyclopropyl)isoxazole | 3 | |
| A31 | (CH$_3$)$_2$CHCH$_2$CH(CH$_3$)— | H | H | O | 3-(cyclopropyl)isoxazole | 3 | |
| A32 | Cl$_2$C(cyclopropyl)CH—CH$_2$— | H | H | O | 3-(cyclopropyl)isoxazole | 3 | |
| A33 | CH$_3$CH$_2$CH(CH$_3$)— | H | H | O | 2-(cyclopropyl)oxadiazole | 2 | 0.98 (t), 1.50–1.82 (m), 2.11–2.24 (m) |
| A34 | CH$_3$CH$_2$CH(CH$_3$)— | H | H | S | 2-(cyclopropyl)oxadiazole | 2 | |
| A35 | CH$_3$CH$_2$CH(CH$_3$)— | H | H | SO$_2$ | 2-(cyclopropyl)oxadiazole | 2 | |
| B36 | (CH$_3$)$_2$CHCH$_2$CH(CH$_3$)— | H | H | O | 2-(cyclopropyl)oxadiazole | 2 | |
| B37 | (CH$_3$)$_2$CH— | H | H | O | 2-(cyclopropyl)oxadiazole | 2 | |
| B38 | CH$_3$OCH$_2$CH$_2$— | H | H | O | 2-(cyclopropyl)oxadiazole | 2 | |

TABLE 7-continued

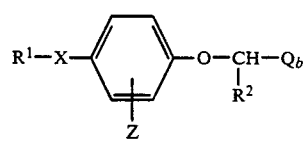

| No. | R$^1$ | R$^2$ | Z | X | Q$_b$ | Substitution in position ... of Q$_b$ | 250 MHz $^1$H-NMR [ppm] in CDCl$_3$ (characteristic signals) |
|---|---|---|---|---|---|---|---|
| B39 | CH$_3$OCH$_2$CH(CH$_3$)— | H | H | O | oxadiazoline with cyclopropyl | 2 | |
| B40 | Cl$_2$C=C(CH$_2$)CH—CH$_2$— (dichlorovinylcyclopropylmethyl) | H | H | O | oxadiazoline with cyclopropyl | 2 | |
| B41 | CH$_3$CH$_2$CH(CH$_3$)— | H | H | O | thiadiazoline-OEt | 5 | 1.27 (d), 1.50 (t), 5.24 (s) |
| B42 | CH$_3$CH$_2$CH(CH$_3$)— | H | H | S | thiadiazoline-OEt | 5 | 1.20 (d), 1.47 (t), 5.28 (s) |
| B43 | CH$_3$CH$_2$CH(CH$_3$)— | H | H | SO$_2$ | thiadiazoline-OEt | 5 | |
| B44 | (CH$_3$)$_2$CHCH$_2$CH(CH$_3$)— | H | H | O | thiadiazoline-OEt | 5 | 1.24 (d), 1.32 (t), 5.25 (s) |
| B45 | (CH$_3$)$_2$CH— | H | H | O | thiadiazoline-OEt | 5 | 1.29 (d), 1.45 (t), 5.24 (s) |
| B46 | Cl$_2$C=C(CH$_2$)CH—CH$_2$— | H | H | O | thiadiazoline-OEt | 5 | 1.48 (t), 2.03–2.19 (m), 5.33 (s) |
| B47 | CH$_3$OCH$_2$CH(CH$_3$)— | H | H | O | thiadiazoline-OEt | 5 | 1.26 (d), 1.47 (t), 5.25 (s) |
| B48 | CH$_3$OCH$_2$CH$_2$— | H | H | O | thiadiazoline-OEt | 5 | 1.46 (t), 3.47 (s), 5.28 (s) |
| B49 | CH$_3$CH$_2$CH(CH$_3$)— | H | H | O | 2-bromothiophene | 5 | 0.99 (t), 1.28 (d), 5.09 (s) |
| B50 | CH$_3$CH$_2$CH(CH$_3$)— | H | H | S | 2-bromothiophene | 5 | 1.22 (d), 1.37–1.58 (m), 6.71–6.96 (m) |

TABLE 7-continued

R¹—X—⟨C₆H₄⟩—O—CH(R²)—Q_b, with Z on ring

| No. | R¹ | R² | Z | X | Q_b | Substitution in position ... of Q_b | 250 MHz ¹H-NMR [ppm] in CDCl₃ (characteristic signals) |
|---|---|---|---|---|---|---|---|
| B51 | CH₃CH₂CH(CH₃)— | H | H | SO₂ | 2-bromothien-5-yl | 5 | |
| B52 | (CH₃)₂CHCH₂CH(CH₃)— | H | H | O | 2-bromothien-5-yl | 5 | 1.63–1.91 (m), 4.23–4.38 (m), 5.02 (s) |
| B53 | (CH₃)₂CH— | H | H | O | 2-bromothien-5-yl | 5 | 4.45–4.52 (m), 5.08 (s), 6.71–6.92 (m) |
| B54 | CH₃OCH₂CH₂— | H | H | O | 2-bromothien-5-yl | 5 | 3.47 (s), 3.70–3.78 (m), 4.02–4.10 (m) |
| B55 | CH₃OCH₂CH(CH₃)— | H | H | O | 2-bromothien-5-yl | 5 | 1.26 (d), 3.39 (s), 5.04 (s) |
| B56 | Cl₂C(cyclopropyl)CH₂— | H | H | O | 2-bromothien-5-yl | 5 | 1.37 (t), 2.05–2.17 (m), 4.07 (d) |
| B57 | CH₃CH₂CH(CH₃)— | H | H | O | 3-(cyclopropyl)-1-methyl-pyrazol-5-yl | 5 | |
| B58 | CH₃CH₂CH(CH₃)— | H | H | S | 3-(cyclopropyl)-1-methyl-pyrazol-5-yl | 5 | |
| B59 | CH₃CH₂CH(CH₃)— | H | H | O | 5-(cyclopropyl)-1-methyl-pyrazol-3-yl | 3 | 1.24 (d), 3.85 (s), 4.91 (s) |
| B60 | CH₃CH₂CH(CH₃)— | H | H | S | 5-(cyclopropyl)-1-methyl-pyrazol-3-yl | 3 | 3.83 (s), 4.92 (s), 5.94 (s) |

TABLE 7-continued

R¹—X—[phenyl(Z)]—O—CH(R²)—Q_b

| No. | R¹ | R² | Z | X | Q_b | Substitution in position ... of Q_b | 250 MHz ¹H-NMR [ppm] in CDCl₃ (characteristic signals) |
|---|---|---|---|---|---|---|---|
| B61 | CH₃CH₂CH(CH₃)— | H | H | SO₂ | 1-methyl-pyrazol-3-yl-cyclopropyl | 3 | |
| B62 | (CH₃)₂CHCH₂CH(CH₃)— | H | H | O | 1-methyl-pyrazol-3-yl-cyclopropyl | 3 | 1.22 (d), 3.87 (s), 4.92 (s) |
| B63 | Cl₂C-CH₂-CH(cyclopropyl)— | H | H | O | 1-methyl-pyrazol-3-yl-cyclopropyl | 3 | 2.03–2.19 (m), 4.93 (s), 5.95 (s) |
| B64 | CH₃OCH₂CH₂— | H | H | O | 1-methyl-pyrazol-3-yl-cyclopropyl | 3 | 3.43 (s), 4.93 (s), 5.93 (s) |
| B65 | CH₃OCH₂CH(CH₃)— | H | H | O | 1-methyl-pyrazol-3-yl-cyclopropyl | 3 | 1.28 (d), 3.89 (s), 5.94 (s) |
| B66 | (CH₃)₂CH— | H | H | O | 1-methyl-pyrazol-3-yl-cyclopropyl | 3 | 1.29 (d), 4.92 (s), 5.93 (s) |
| B67 | CH₃CH₂CH(CH₃)— | H | H | O | 2-methyl-thiazol-4-yl | 4 | |
| B68 | (CH₃)₂CHCH₂CH(CH₃)— | H | H | O | 2-methyl-thiazol-4-yl | 4 | |
| B69 | CH₃CH₂CH(CH₃)— | H | H | O | isoxazol-5-yl-cyclopropyl | 5 | 1.50–1.82 (m), 2.04–2.18 (m), 5.13 (s) |

TABLE 7-continued

R¹—X—[phenyl with Z]—O—CH(R²)—Q_b

| No. | R¹ | R² | Z | X | Q_b | Substitution in position ... of Q_b | 250 MHz ¹H-NMR [ppm] in CDCl₃ (characteristic signals) |
|---|---|---|---|---|---|---|---|
| B70 | CH₃CH₂CH(CH₃)— | H | H | S | (cyclopropyl-isoxazoline) | 5 | |
| B71 | Cl₂C(CH)(CH₂)CH—CH₂— | H | H | O | (cyclopropyl-isoxazoline) | 5 | |
| B72 | (CH₃)₂CHCH₂CH(CH₃)— | H | H | O | (cyclopropyl-isoxazoline) | 5 | |
| B73 | CH₃CH₂CH(CH₃)— | H | H | O | 2-Cl-thiophene | 4 | 1.52–1.84 (m), 4.93 (s), 7.08 (s) |
| B74 | CH₃CH₂CH(CH₃)— | H | H | O | 3-CH₃-thiophene | 2 | 0.98 (t), 1.51–1.82 (m), 2.28 (s) |
| B75 | CH₃CH₂CH(CH₃)— | H | H | O | thiophene | 2 | 5.10 (s), 6.72–7.06 (m), 7.28–7.32 (m) |
| B76 | CH₃CH₂CH(CH₃)— | H | H | O | thiophene | 3 | 4.12–4.28 (m), 5.05 (s), 7.30–7.41 (m) |
| B77 | CH₃CH₂CH(CH₃)— | H | H | O | 2,3-Br₂-thiophene | 4 | 4.01–4.24 (m), 4.88 (s), 7.32 (s) |
| B78 | CH₃CH₂CH(CH₃)— | H | H | O | 2,3-Cl₂-thiophene | 4 | 1.48–1.82 (m), 6.75–6.98 (m), 7.18 (s) |
| B79 | CH₃CH₂CH(CH₃)— | H | H | O | 3-CH₃-oxadiazole | 2 | 1.23 (d), 2.52 (s), 5.12 (s) |
| B80 | CH₃CH₂CH(CH₃)— | H | H | O | cyclopropyl-thiazole | 4 | |

TABLE 7-continued $$R^1-X-\underset{Z}{\underset{|}{C_6H_3}}-O-\underset{R^2}{\underset{|}{CH}}-Q_b$$

| No. | R¹ | R² | Z | X | Q_b | Substitution in position ... of Q_b | 250 MHz ¹H-NMR [ppm] in CDCl₃ (characteristic signals) |
|---|---|---|---|---|---|---|---|
| B81 | CH₃CH₂CH(CH₃)– | H | H | S | 2-(cyclopropyl)thiazole | 4 | |
| B82 | (CH₃)₂CHCH₂CH(CH₃)– | H | H | O | 2-(cyclopropyl)thiazole | 4 | |
| B83 | Cl₂C(CH₂)CHCH₂– (dichlorocyclopropyl-methyl) | H | H | O | 2-(cyclopropyl)thiazole | 4 | |
| B84 | CH₃OCH₂CH₂– | H | H | O | 2-(cyclopropyl)thiazole | 4 | |
| B85 | CH₃CH₂CH(CH₃)– | CH₃ | H | O | 3-(cyclopropyl)isoxazole | 5 | |
| B86 | CH₃CH₂CH(CH₃)– | H | 2-F | O | 3-(cyclopropyl)isoxazole | 5 | |
| B87 | CH₃CH₂CH(CH₃)– | H | 2-F | O | 2-ethoxy-1,3,4-thiadiazole | 5 | |
| B88 | CH₃CH₂CH(CH₃)– | H | H | O | 2-(cyclopropyl)-1,3,4-thiadiazole | 2 | 1.26 (d), 2.32–2.47 (m), 5.39 (s) |
| B89 | CH₃CH₂CH(CH₃)– | H | H | S | 2-(cyclopropyl)-1,3,4-thiadiazole | 2 | 1.20 (d), 2.32–2.65 (m), 5.42 (s) |
| B90 | CH₃CH₂CH(CH₃)– | H | H | SO₂ | 2-(cyclopropyl)-1,3,4-thiadiazole | 2 | |

TABLE 7-continued

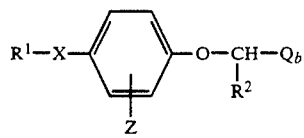

| No. | R¹ | R² | Z | X | $Q_b$ | Substitution in position ... of $Q_b$ | 250 MHz ¹H-NMR [ppm] in CDCl₃ (characteristic signals) |
|---|---|---|---|---|---|---|---|
| B91 | (CH₃)₂CHCH₂CH(CH₃)— | H | H | O | N—N, S, CH, CH₂, CH₂ (thiadiazoline-cyclopropyl) | 2 | 1.23 (d), 2.32–2.66 (m), 5.38 (s) |
| B92 | Cl₂C(CH₂)CH—CH₂— (dichlorocyclopropyl-methyl) | H | H | O | " | 2 | 2.01–2.19 (m), 2.32–2.47 (m), 5.39 (s) |
| B93 | CH₃OCH₂CH₂— | H | H | O | " | 2 | 2.28–2.48 (m), 3.43 (s), 5.34 (s) |
| B94 | CH₃OCH₂CH(CH₃)— | H | H | O | " | 2 | 1.28 (d), 2.34–2.48 (m), 5.40 (s) |
| B95 | (CH₃)₂CH— | H | H | O | " | 2 | 1.30 (d), 2.31–2.48 (m), 5.38 (s) |
| B96 | CH₃—(CH₂)₂CH(CH₂CH₃)— | H | H | O | " | 2 | 2.32–2.47 (m), 3.98–4.12 (m), 5.35 (s) |

USE EXAMPLES FOR N-PHENOXYMETHYL-SUBSTITUTED AZOLES IA

In the examples that follow, the action of compounds according to the invention, or agents containing them, on pests was compared with that of the following prior art compounds. The purity of the substances and of the comparative agents was in excess of 95%.

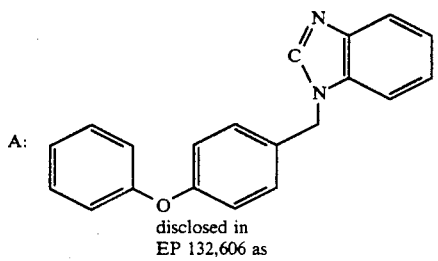

A: disclosed in EP 132,606 as compound no. 1

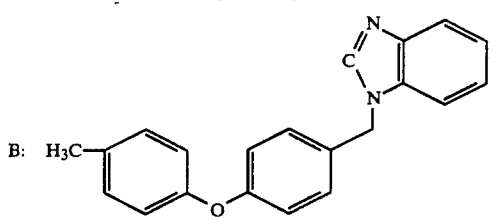

B: disclosed in EP 132,606 as compound no. 8

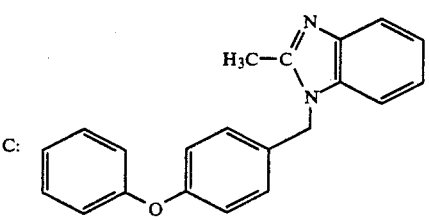

C:

-continued disclosed in
EP 132,606 as
compound no. 29

The concentrations at which the candidate compounds exhibit 100% kill or inhibition are the minimum concentrations. At least two experiments were run for each concentration and an average was formed.

EXAMPLE A.A

*Dysdercus intermedius* (cotton stainer), ovicidal action

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel.

The eggs were then dipped for 5 seconds into aqueous formulations of the active ingredients and excess liquid was allowed to drip off onto filter paper, care being taken to prevent the eggs coming into contact with the paper. The markers were placed (adhesive tape up) in plastic pallets. Half a roll of absorbent cotton was moistened with water and placed in each beaker to prevent drying out, and the pallets were covered with a glass plate.

Assessment took place after about 8 days (after the larvae in the control batch had hatched). Hatch inhibition was assessed in %.

In this experiment, the compounds of Examples A1, A4, A20, A42 and A60 achieved 80% hatch inhibition at concentrations of 100 ppm and less, whereas comparative agents A, B and C did not inhibit hatching at a concentration of 1,000 ppm.

EXAMPLE B.A

*Dysdercus intermedius* (cotton stainer); breeding experiment

Petri dishes 10 cm in diameter were lined with 1 ml of acetonic solutions of the active ingredients. After the solvent had evaporated, 20 larvae of the penultimate stage were placed in each dish.

After 24 hours, the surviving animals were transferred to 1 liter jars containing 200 g of sterile sand (particle size: 0 to 3 mm). Prior to the experiment, 25 ml of aqueous active ingredient formulations were poured onto this sand.

The food proffered was swollen cotton seeds, which were changed weekly. The sand was moistened with pure water—again once a week.

The temperature was kept at 25° to 27° C. The jars were monitored until the eggs in the control batch hatched.

In this experiment, the compounds of Examples A1, A4, A5, A20, A42 and A60 achieved a kill rate of 100% at a concentration of 10 ppm and less, whereas the comparative agents were virtually ineffective at a concentration of 25 ppm, i.e., achieved a kill rate of less than 60%. Use examples for phenoxyalkyl-substituted heteroaromatics bearing a 5-membered ring In the examples that follow, the action of compounds according to the invention, or agents containing them, on pests was compared with that of the following prior art compounds:

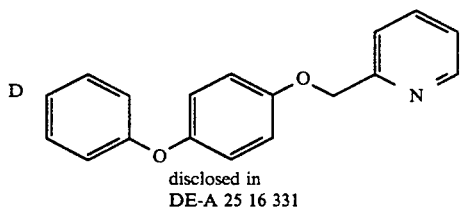

disclosed in
DE-A 25 16 331

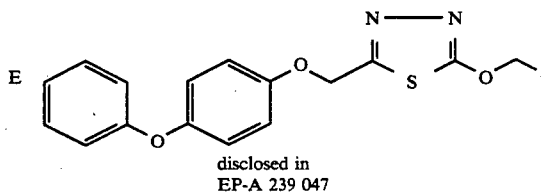

disclosed in
EP-A 239 047

The purity of the comparative agents and of the compounds according to the invention was at least 90 to 95%. The concentrations at which the candidate compounds exhibit 100% kill or inhibition are the minimum concentrations. At least two experiments were run for each concentration.

*Dysdercus intermedius* (cotton stainer), ovicidal action

Pieces of adhesive tape (about 0.8 cm) were stuck to the top edge of plastic plant markers. 24 hours before commencement of the experiment, eggs of the cotton stainer contained in a vessel were attached to the adhesive strips by dipping the markers into the vessel.

The eggs were then dipped for 5 seconds into aqueous formulations of the active ingredients and excess liquid was allowed to drip off onto filter paper, care being taken to prevent the eggs coming into contact with the paper.

The markers were placed (adhesive tape up) in plastic pallets. Half a roll of absorbent cotton was moistened with water and placed in each beaker to prevent drying out, and the pallets were covered with a glass plate.

Assessment took place after about 8 days (after the larvae in the control batch had hatched). Hatch inhibition was assessed in %. In this experiment, compounds B1, B4 and B7 achieved 80% hatch inhibition at concentrations of 400 ppm and less, whereas comparative agent D did not inhibit hatching at a concentration of 1,000 ppm.

EXAMPLE B.B

*Caenorhaditis elegans* (nematodes); contact experiment 0.5 ml of acetonic solutions of the active ingredients was applied to the surface of a nutrient medium (5 ml in plastic Petri dishes 35 mm in diameter and 10 mm high). After the acetone had evaporated, the medium was infected with 30 µl of E-coli bacteria and 50 µl of nematode suspension. After 48 hours, the contact action was assessed in % kill.

At an active ingredient concentration of 100 ppm, the compounds of Examples B2, B3, B4, B5 and B49 achieved a kill rate of 100%, whereas comparative agents D and E were virtually ineffective at this concentration, i.e., achieved a kill of less than 60%.

We claim:

1. Phenoxyalkyl-substituted heteroaromatics of the formula Ib

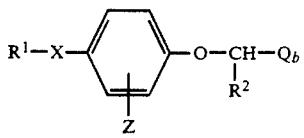 (Ib)

where the substituents have the following meanings: $R^1$ $C_1$-$C_{12}$ alkyl, $C_2$-$C_{12}$-alkenyl, $C_2$-$C_{12}$-alkynyl, $C_1$-$C_{12}$-haloalkyl, $C_2$-$C_{12}$-haloalkenyl, $C_2$-$C_{12}$-haloalkynyl, $C_3$-$C_{12}$-alkoxyalkyl, $C_3$-$C_8$-cycloalkyl, $C_4$-$C_{12}$-cycloalkylalkyl, $C_3$-$C_8$-halocycloalkyl, $C_4$-$C_{12}$-halocycloalkylalkyl, $C_4$-$C_{12}$-cycloalkylhaloalkyl or $C_4$-$C_{12}$-halocycloalkylhaloalkyl;

X O, S or $SO_2$;

Z hydrogen, halogen or $C_1$-$C_4$-alkyl;

$R^2$ hydrogen or $C_1$-$C_4$-alkyl; and $Q_b$ isoxazol-3-yl or isoxazol-5-yl which is unsubstituted or mono- or polysubstituted by halogen, $C_1$-$C_8$-alkyl, $C_2$-$C_8$-alkenyl, $C_1$-$C_4$-haloalkyl, $C_1$-$C_8$-alkoxy, $C_1$-$C_8$-alkylthio, $C_2$-$C_8$-alkoxyalkyl or $C_3$-$C_{10}$-cycloalkyl.

2. An agent for combating insects, mites and nematodes containing a phenoxyalkyl-substituted 5-membered heteroaromatic of the formula Ib as set forth in claim 1, and conventional carriers.

3. A process for combating insects, mites and nematodes, wherein an insecticidally, mitically and nematodically effective amount of a phenoxyalkyl-substituted 5-membered heteroaromatic of the formula Ib as set forth in claim 1 is allowed to act on insects, mites and nematodes or their habitat.

4. Phenoxyalkyl-substituted heteroaromatics according to claim 1, wherein in the formula (Ib) $R^1$ is

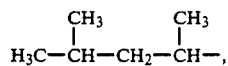

$R^2$ is H, Z is H and X is O.

5. An agent for combating insects, mites, and nematodes according to claim 2, wherein in the formula (Ib) $R^1$ is

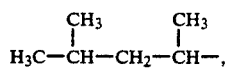

$R^2$ is H, Z is H and X is O.

6. The process for combating insects, mites and nematodes according to claim 3, wherein in the formula (Ib) $R^1$ is

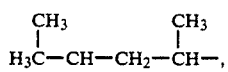

$R^2$ is H, Z is H and X is O.

* * * * *